United States Patent [19]

Destouet et al.

[11] Patent Number: 4,995,882
[45] Date of Patent: Feb. 26, 1991

[54] RADIOLUCENT BREAST IMPLANT

[75] Inventors: Judy M. Destouet, St. Louis; John O. Eichling, Marthasville; Louis A. Gilula, St. Louis; Barbara S. Monsees, St. Louis; Vernon L. Young, St. Louis, all of Mo.

[73] Assignee: Washington University

[21] Appl. No.: 399,180

[22] Filed: Aug. 28, 1989

[51] Int. Cl.$^5$ ............................................. A61F 2/12
[52] U.S. Cl. ......................................................... 623/8
[58] Field of Search ........................................ 623/8, 7

[56] References Cited

U.S. PATENT DOCUMENTS

| | | | |
|---|---|---|---|
| 3,934,274 | 1/1976 | Hartley, Jr. | 623/8 |
| 4,610,690 | 9/1986 | Tiffany | 623/8 |
| 4,731,081 | 3/1988 | Tiffany et al. | 623/8 |

*Primary Examiner*—Ronald Frinks

[57] ABSTRACT

A radiolucent breast implant is comprised of a silicon envelope filled with any biocompatible triglyceride such as peanut oil or sunflower seed oil, or any other material having an effective atomic number of 5.9 which is the effective atomic number of fat, the major component of a human breast. Such a breast implant is radiolucent in that it duplicates the photoelectric interaction of fat which is the major effect producing subject contrast at low radiation levels as used in mammography. A radiolucent breast implant dramatically improves the usefullness of mammography in detecting tumors in patients having breast implants and may also result in a lower radiation dose for each examination.

14 Claims, No Drawings

RADIOLUCENT BREAST IMPLANT

BACKGROUND AND SUMMARY OF THE INVENTION

Since the development of silicone gel filled breast implants, over one million American women have undergone augmentation mammoplasty. Although various materials have been used experimentally, the predominant breast implant has been a silicone envelope filled with a silicone gel. It is well known that these silicone gel filled implants are radiodense or radiopaque and hence obscure significant portions of the glandular tissue during mammography. In recent years because of a ten percent lifetime risk that a woman will develop breast cancer, various X-ray techniques have been developed and improved to make mammography a safe and effective diagnostic tool in the early detection of breast cancer. These efforts are hindered for those women who have undergone augmentation mammoplasty with silicone gel filled implants.

A useful mammogram produces a radiograph that exhibits variations in the photographic density film in order to demonstrate meaningful information. Radiologists refer to the photographic density variations (a quantitative measure of film darkening) as film contrast. Film contrast is created by the differential attenuation of the X-ray beam that penetrates the body part being examined. Film contrast can be augmented or enhanced by the characteristics of the film but subject contrast, i.e. differential attenuation of the X-ray beam, must be present in order to obtain clinically useful information. An X-ray film is simply a spatial recording or mapping of the relative number of X-rays passing through the examined body part without any interaction. Subject contrast through differential attenuation occurs because some materials, e.g. bone, are more opaque to X-rays than other materials, e.g. muscle, fat, etc., thereby creating shadows of varying intensity in the radiograph which may be interpreted by skilled radiologists.

In the diagnostic radiology range of X-ray photon energies, only two interactions are effective in attenuating X-rays from the incident beam and, thereby, producing the differential attenuation or subject contrast needed to yield sufficient contrast for a useful radiograph. These two types of X-ray interactions are called Compton scattering and photoelectric effect or interaction. It is well known that Compton scattering yields little radiographic contrast and hence is generally not useful for conventional X-ray examinations. This is because the Compton scattering effect is generally related to the electron density (electrons per gram) of the material being viewed. Electron density has been defined as $N_oZ/A$ where $N_o$ is Avogadro's number, Z is the atomic number of the constituent element, and A is the atomic weight of the constituent element. The only significant exception to a general homogeneity of electron density within body constituents is hydrogen which has twice as many electrons per gram as most elements found in the human body. Hence, subtle variations in the electron densities of hydrogen-rich materials, e.g. fat, can be effectively mapped in computed tomography because of the Compton interaction.

The same cannot be said for the second kind of interaction, photoelectric effect. This is because the photoelectric effect varies approximately with the cube of the element's atomic number. In other words, comparing lead with aluminum, the photoelectric interaction with lead is about 250 times more likely than with aluminum as lead has an atomic number (Z) of 82 while aluminum has an atomic number (Z) of 13 and, by comparison, $(82/13)^3$ is approximately equal to 251.

Others have developed techniques for predicting the photoelectric effect occurring in mixtures of compounds, relying on a number defined as the effective atomic number. This effective atomic number can be defined as $$Z_{eff} = \sqrt[2.94]{a_1 Z_1^{2.94} + a_2 Z_2^{2.94} + a_3 Z_3^{2.94} + \ldots}$$

where $a_1$, $a_2$, $a_3$, etc. are the electron fractions bound in the constituent elements having corresponding atomic numbers of $Z_1$, $Z_2$, $Z_3$, etc. which comprise the compound. For water, the effective atomic number can be computed as 7.41 which means that water induces a photoelectric interaction much as would an element having an atomic number between nitrogen (Z=7) and oxygen (Z=8).

As indicated above, subject contrast in mammography is a particular problem especially in attempting to demonstrate a small cluster of microcalcifications in a relatively large tissue bed which might be indicative of cancer. Mammography is best performed at low X-ray energies since the photoelectric interaction is predominant over Compton scattering only at low X-ray energies. As silicone has an effective atomic number of 10.4, and fat which is generally the composition of breast tissue has an effective atomic number of 5.9, silicone implants are radiographically opaque and will obscure any information that would have otherwise been evident in the tissues below or above the silicone. This problem has forced radiologists to obtain additional special views in patients with implants in an attempt to image as much breast tissue as possible. Unfortunately, these additional views increase the total radiation dose required for each examination which, in itself, presents an increased health risk.

Mammograms are performed with a phototimer which is a radiation sensor placed beneath the film screen cassette that automatically terminates each exposure when sufficient X-rays have been transmitted to yield an appropriately darkened film after development. The use of the phototimer assists in achieving consistent film density for various size breasts and it helps to eliminate retakes. However, if a portion of a silicone gel implant intercepts the radiation monitored by the phototimer (a recent report stated that the implant often accounts for as much as 60% of the imaged area) then the exposure time will be much longer and the radiation dose to the overlying breast tissues can be several times higher than if the implant had not been present. Hence, the silicone gel implant not only prevents the imaging of overlying and underlying breast anatomy, but in some cases results in a substantially higher radiation dose to the overlying tissues for each exposure. Because of this, the phototimer cannot be used and even an experienced technologist must use trial and error to achieve the proper exposure. There is a further problem with augmented breasts that relates to the way a routine mammogram is performed. Normally, the breast is compressed between two plates which flattens the breast and enables a more uniform exposure. A subset of women with implants develop a condition known as "capsular contracture". This is a reaction to the implant that results in a fibrotic capsule surrounding the implant rendering it noncompressible. In these patients, specialized views are difficult if not impossible to obtain. If the implant is radiolucent, even in the presence of a capsular contracture, a useful mammogram can be performed.

To solve these and other problems, the inventors herein have succeeded in developing a breast implant which is essentially radiolucent in terms of having the same photoelectric interaction as body fat, the material which comprises the predominant tissue in a normal breast. While any filler material can be used having an effective atomic number of 5.9, the inventors have found that any biocompatible triglyceride which has an effective Z value of 5.9 and which is closest to carbon (Z=6) is preferred. Examples of a suitable filler include peanut oil and sunflower seed oil. Present techniques well known to those of ordinary skill in the art for breast implant manufacturing may be used to implement the invention including using a silicone envelope having a substantially thin wall as it does not dramatically alter the effective atomic number of the implant as a whole. Thus, the inventors' breast implant can be utilized immediately using existing and well known techniques to achieve implantation.

The inventors have also found that filler material having a physical density approximately the same as that of breast glandular material improves the radiolucent quality of the implant.

It is not believed that a drawing is required as an aid to understanding the present invention and, hence, none is being offered.

DETAILED DESCRIPTION OF THE PREFERRED EMBODIMENT

The inventors' preferred embodiment for achieving a breast implant which is essentially radiolucent comprises a silicone envelope as is well known to those of ordinary skill in the breast implant art, said silicone envelope being filled with any biocompatible triglyceride, such as peanut oil or sunflower seed oil. The silicone envelope may be sealed as is presently done in the prior art and inserted using techniques and skills well known in the art of augmentation mammoplasty. While the inventors' preferred embodiment comprises peanut oil or sunflower seed oil, any other biocompatible filler material can be used which has an effective atomic number of 5.9, the effective atomic number of fat, which comprises the major element in breast glandular tissue, and which is close to the atomic number for carbon (Z=6).

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A breast implant having an average radiographic density substantially the same as that of a human breast and being substantially radiolucent throughout its entirety.

2. The breast implant of claim 1 wherein said implant is substantially comprised of material having an effective atomic number approximately the same as that of breast glandular material.

3. The breast implant of claim 2 wherein said effective atomic number is approximately 5.9.

4. The breast implant of claim 2 wherein said implant material has a physical density approximately the same as that of breast glandular material.

5. The breast implant of claim 4 wherein said implant is comprised of a fluid contained within a flexible envelope, the fluid and envelope being made of different materials.

6. The breast implant of claim 5 wherein said envelope is made of silicone and the filler is a biocompatible triglyceride.

7. The breast implant of claim 6 wherein the filler is peanut oil.

8. The breast implant of claim 6 wherein the filler is sunflower seed oil.

9. A breast implant comprised of a material having an effective atomic number substantially the same as that of breast glandular material and being substantially radiolucent throughout its entirety.

10. The breast implant of claim 9 wherein the effective atomic number is approximately 5.9.

11. A breast implant comprised of a material having a physical density substantially the same as that of breast glandular material and being substantially radiolucent throughout its entirety.

12. A breast implant, said breast implant being substantially radiolucent throughout its entirety when surrounded by breast tissue, said breast implant being comprised of a filler material contained within an envelope, said filler material being comprised of a biocompatible triglyceride.

13. A breast implant, said breast implant being substantially radiolucent throughout its entirety so that surrounding and underlying breast tissue is readily viewable using accepted radiographic techniques, intensities, and protocols.

14. The breast implant of claim 13 wherein said implant is filled with a bio-compatible triglyceride.

* * * * *